United States Patent [19]

Grall et al.

[11] Patent Number: 4,596,007
[45] Date of Patent: Jun. 17, 1986

[54] INTERFEROMETRIC SONAR IN NON-LINEAR ACOUSTICS

[75] Inventors: Georges Grall, Le Conquet; Francois Peynaud, Brest, both of France

[73] Assignee: Thomson-CSF, Paris, France

[21] Appl. No.: 541,313

[22] Filed: Oct. 12, 1983

[30] Foreign Application Priority Data

Oct. 12, 1982 [FR] France ................................ 82 17071

[51] Int. Cl.$^4$ ............................................. G01S 15/87
[52] U.S. Cl. ...................................... 367/92; 367/105
[58] Field of Search ...................... 367/87, 92, 99, 105, 367/905

[56] References Cited

U.S. PATENT DOCUMENTS

| | | | |
|---|---|---|---|
| 3,613,069 | 10/1971 | Cary, Jr. | 367/92 |
| 3,716,824 | 2/1973 | Dorr et al. | 367/88 |
| 3,786,405 | 1/1974 | Chramiec et al. | 367/92 |
| 3,824,531 | 7/1974 | Walsh | 367/92 |
| 4,081,783 | 3/1978 | Honda | 367/101 |
| 4,234,939 | 11/1980 | Grall | 367/87 |

*Primary Examiner*—Richard A. Farley
*Attorney, Agent, or Firm*—Cushman, Darby & Cushman

[57] ABSTRACT

An interferometric sonar in non-linear acoustics for high-resolution observations of objects located in the vicinity of the sea floor includes two end transducers for simultaneous transmission at two high frequencies $F_1$ and $F_2$ of the order of 200 kHz. Reception is performed by hydrophones placed between the sending transducers at the low frequency $F_2-F_1$ of the order of 20 kHz. Angular channels are formed during two transmission sequences. Transmission takes place in phase at the frequency $F_2-F_1$ in one sequence and in phase opposition in the other sequence in the case of the two sources generated by non-linear effects.

7 Claims, 8 Drawing Figures

INTERFEROMETRIC SONAR IN NON-LINEAR ACOUSTICS

BACKGROUND OF THE INVENTION

This invention relates to an interferometric sonar which utilizes the non-linear properties of a sea-water environment. In underwater acoustics, the search for objects such as mines on the sea floor calls for the use of a high-resolution sonar in order to identify such objects. Moreover, searching for mines is advantageously carried out at frequencies of a few tens of kHz (designated as low frequencies) in order to permit detection and location of buried mines. Acoustic energy in fact penetrates to a significant extent into sands and sediments only at frequencies which do not exceed 30 kHz. Furthermore, mines may be covered with so-called anechoic materials for absorbing sound waves but these materials are very effective only at high frequencies.

The use of low frequencies with good resolution calls for sonar transducer arrays of substantial size or synthetic antennas sonar transducer arrays involving complex technology.

As disclosed in particular in U.S. Pat. No. 4,234,939 (incorporated herein by reference), it is known to construct a high-resolution active sonar having a receiving transducer array comprising an array or hydrophones and a sending transducer comprising two transducers placed at the ends of the receiving transducer array. In order to ensure good coverage of an angular sector, transmission by the two end transducers takes place alternately in phase or in phase opposition. It is also a known practice to transmit at two high frequencies and to receive at the difference frequency as a result of non-linearities of the propagation medium.

SUMMARY OF THE INVENTION

The sonar in accordance with the invention permits good resolution by virtue of interferometric transmission at two frequencies and reception at the difference frequency.

It is also possible in accordance with the invention to receive both at high frequency (HF) and at low frequency (LF) and thus to obtain simultaneously items of information which are delivered both by the LF sonar and by the HF sonar. For example, it is thus possible to display these two images on the same screen. By visual correlation, this achieves enhanced detecting capability and a reduced false-alarm ratio.

In brief outline, the invention proposes an interferometric sonar comprising a receiving transducer array having N transducers, a sending transducer array having two transducers placed at the ends of the receiving transducer array. The distinctive feature of the invention lies in the fact that transmission by both transducers takes place simultaneously at two frequencies $F_1$ and $F_2$ or so-called high frequencies, that the signals received at the difference frequency $F_1 - F_2$ or so-called low frequency are applied to a device for the formation of low-frequency channels, that the signals are applied to a visual display device after detection, that the two sending transducers transmit in phase at the frequency $F_2$ and alternately in phase and in phase opposition at the frequency $F_1$, and that the channels formed are centered on the peaks of the successive interferometric diagrams.

DESCRIPTION OF THE PREFERRED EMBODIMENT

It is known that, if two sources radiate in synchronism, the radiation diagram $T_o(\theta)$ in the case of two point sources is given by:

$$T_o(\theta) = \cos\left[\frac{\pi L}{\lambda} \sin\theta\right] \quad (1)$$

where L is the distance between the two sources, $\theta$ is the angle made by a direction with the normal to the straight line which joins said two sources, and $\lambda$ is the wavelength in the propagation medium.

Figure 1:
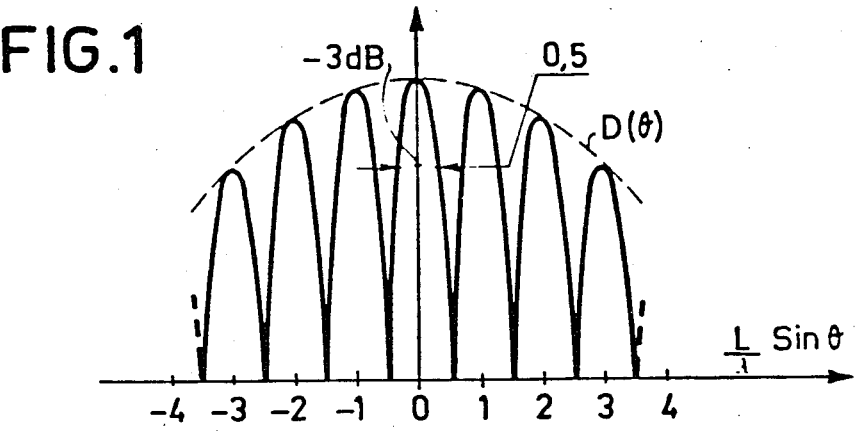
FIGS. 1, 2 and 3 are diagrams of transmission, reception and transmission-reception of an interferometric sonar.

In the case of extended sources, the diagram $T(\theta)$ (FIG. 1) is given by:

$$T(\theta) = T_o(\theta) \cdot D(\theta)$$

where $T_o(\theta)$ is given by relation (1) and $D(\theta)$ is the elementary diagram of each of the two sources.

Figure 2:
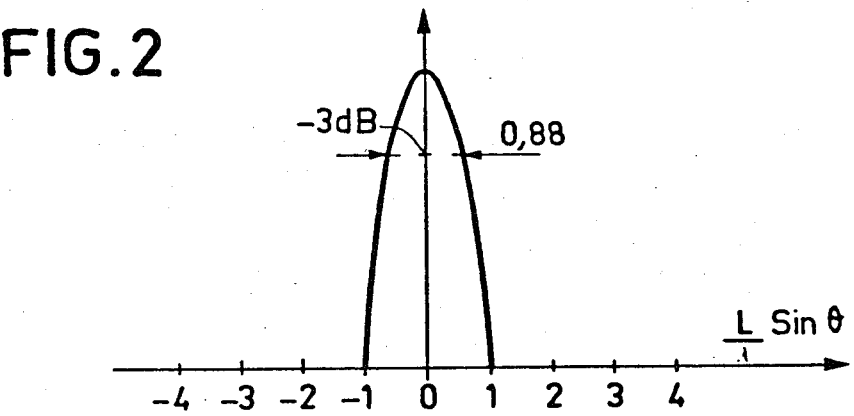

In the case of a receiving transducer array which is also of length L and provided with the transducers considered as continuously occupying said length L or, in practical terms, with a spacing d between transducers such that $d \leq \lambda/2$, the reception diagram $R(\theta)$ is such that:

$$R(\theta) = \frac{\sin\left[\frac{\pi L}{\lambda}\sin\theta\right]}{\frac{\pi L}{\lambda}\sin\theta} \quad (2)$$

with a width of 0.88 $\lambda/L$ at 3 dB as shown in FIG. 2, in which the side lobes have not been considered.

In accordance with the foregoing relations, the transmission-reception diagram $T(\theta) \times R(\theta)$ is as follows:

$$T(\theta) \times R(\theta) = \frac{\sin[(2\pi L \sin\theta)/\lambda]}{(2\pi L \sin\theta)/\lambda} \times D(\theta) \quad (3)$$

Expression (3) shows that the complete diagram has one-half the value at 3 dB, that is to say 0.44 $\lambda/L$, which corresponds in accordance with relation (2) to a diagram for a transducer array length of 2L.

It is already known to process signals received by the transducers in order to form m channels by compensating for the geometric lags corresponding to the m directions determined by angles such that $\theta_i$ with $i < m$. If the angles $\theta_i$ are such that $\sin\theta_i = K_i \lambda/L$, where $K_i$ is an integer constant, the peak values for the formed channels correspond to those of the function $T_o(\theta)$ of relation (1).

Figure 3:
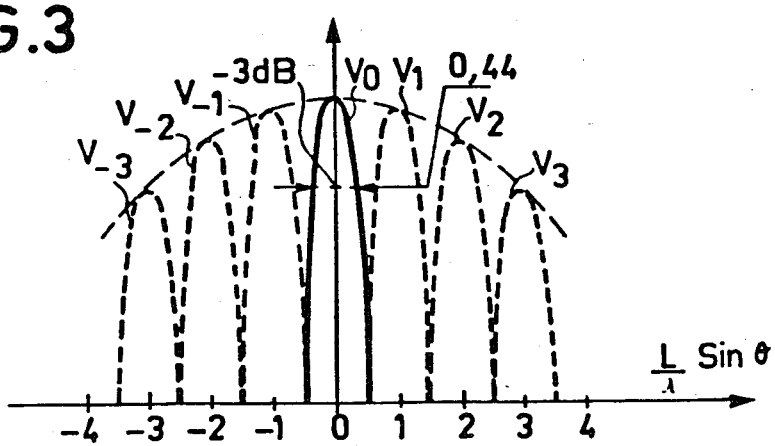

FIG. 3 shows the central channel $V_0$ and the six channels $V_{-3}$, $V_{-2}$, $V_{-1}$, $V_1$, $V_2$ and $V_3$ which are centered on the values of $(L \sin \theta)/\lambda = -3, -2, -1, 1, 2$ and $3$.

Since said formed channels leave gaps between them, these gaps are filled-up by carrying out alternate transmissions in which the two transducers are in phase and then in phase opposition. In the latter case, there is obtained in respect of $T_o(\theta)$:

$$T_o(\theta) = \sin[(\pi L/\sin \theta)/\lambda] \qquad (4)$$

and m other channels are formed in m directions determined by the angles $\theta_i$ such that $\sin \theta_i = (K_i = \tfrac{1}{2})\lambda/L$. These channels are interposed between the channels shown in FIG. 3.

Figure 4:
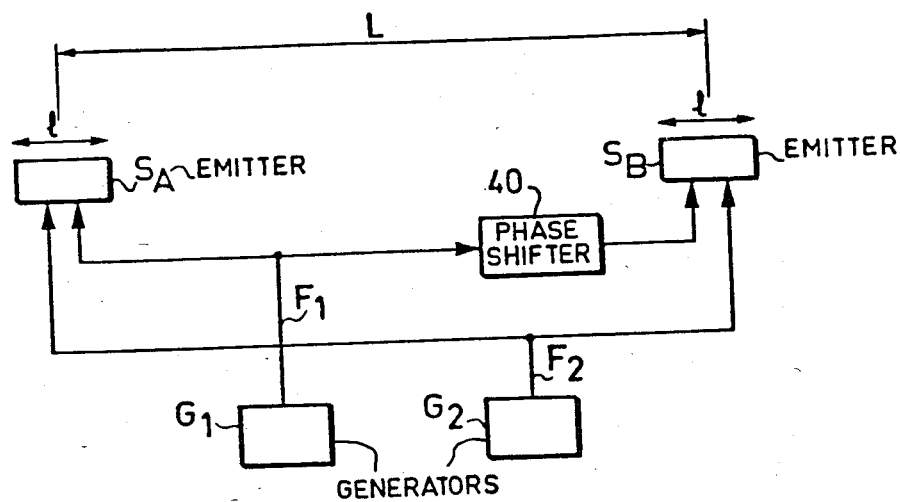
FIG. 4 is a diagram of an interferometric sending antenna.
Figure 5:
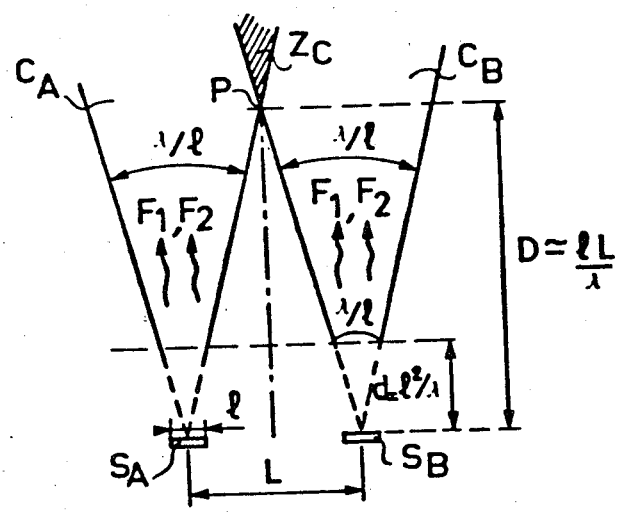
FIG. 5 is an explanatory diagram in the case of non-linear transmission.

A sending transducer array in accordance with the invention is shown in FIG. 4. The two sending transducers $S_A$ and $S_B$ are both supplied simultaneously by signals at the high frequencies (HF) $F_1$ and $F_2$ delivered by generators $G_1$ and $G_2$. Beyond the Fresnel zone, the two transducers transmit in the form of cones $C_A$ and $C_B$ (as shown in FIG. 5) having an angular aperture $\lambda/l$ in the plane of the figure, where $\lambda$ is the wavelength associated with the mean frequency $(F_1+F_2)/2$ and l is the length of the two transducers $S_A$ and $S_B$ which are spaced at a distance L.

When an acoustic wave is emitted in water, the non-linear properties of the medium are such that the wave velocity depends on the instantaneous amplitude of the sound pressure, and the sinusoidal shape of said pressure undergoes deformation, thus tending towards a saw-tooth shape.

In consequence, if two sound waves at the so-called primary frequencies $F_1$ and $F_2$ are emitted within the same volume, they interact so as to provide all the intermodulation products including in particular the signal at the frequency $F_2+F_1$ which is rapidly absorbed, and the signal to be obtained at the frequency $F_2-F_1$.

The element which radiates this low frequency is therefore not the transducer array but the entire volume in which sound is emitted at the two primary frequencies. This element of elongated shape and consisting of water radiates its low frequency in the direction of propagation of the primary waves.

It is known that the Fresnel zone extends in practice to the distance $d = l^2/\lambda$ (5). The point of intersection of the two cones $C_A$ and $C_B$ at the point P is at the distance $D = lL/\lambda$ (6) and according to relations (5) and (6), $D/d = L/l$, whence $D/d \gg 1$ since $L \gg l$ and the zone $Z_c$ in which interference takes place at high frequency is located well beyond the Fresnel zone. In consequence, the non-linear interaction generates in the water, at the level of the two emission cones $C_A$ and $C_B$, two low-frequency sources $F_1 - F_2$ spaced at a distance L, the interaction zone $Z_c$ being sufficiently remote to have a negligible influence. A conventional calculation in non-linear acoustics in fact shows that the length of the volume of water intercepted by the two emission cones is sufficient to generate the two low-frequency sources. A low-frequency interferometer in the transmission mode is thus obtained.

A number m of LF (low-frequency) channels are formed in the receiving mode on the transducer array of length L and the transmission-reception product has a low-frequency radiation diagram which is twice as directional as that of a conventional antenna.

Similarly, it must be possible in the case of the HF (high-frequency) interferometer to phase-shift the transmission by $\pi$ in order to form $2m-1$ channels throughout an angular sector. There is shown in FIG. 4 a phase-shifter 40 for the signal at the frequency $F_1$ and transmission takes place alternately with and without a phase-shift by $\pi$ on the signal at the frequency $F_1$. It should be noted that the $\pi$ phase-shift can be applied indifferently either to the signal at the frequency $F_1$ as indicated by way of example or to the signal at the frequency $F_2$.

In one exemplified embodiment of the invention relating to a high-resolution sonar for detection and location of submerged objects with interferometric transmission, the sonar has the following characteristics:
first high-frequency $F_1 = 160$ kHz;
second high-frequency $F_2 = 190$ kHz;
mean high-frequency $(F_1+F_2)/2 = 175$ kHz;
mean HF transmission wavelength $\lambda = 8.57$ mm;
distance between the sending transducers $= 171\lambda \approx 1.5$ m;
dimensions of the sending transducers: length $= 7\lambda \approx 60$ mm; height $= 4\lambda \approx 34$ mm;
LF receiving frequency $F_2 - F_1 = 30$ kHz;
reception wavelength $= 50$ mm.

The receiving antenna is a flat hydrophone base which is sensitive to the low frequency $F_1 - F_2$. The received signals are processed in the conventional manner in order to form channels.

Figure 6:
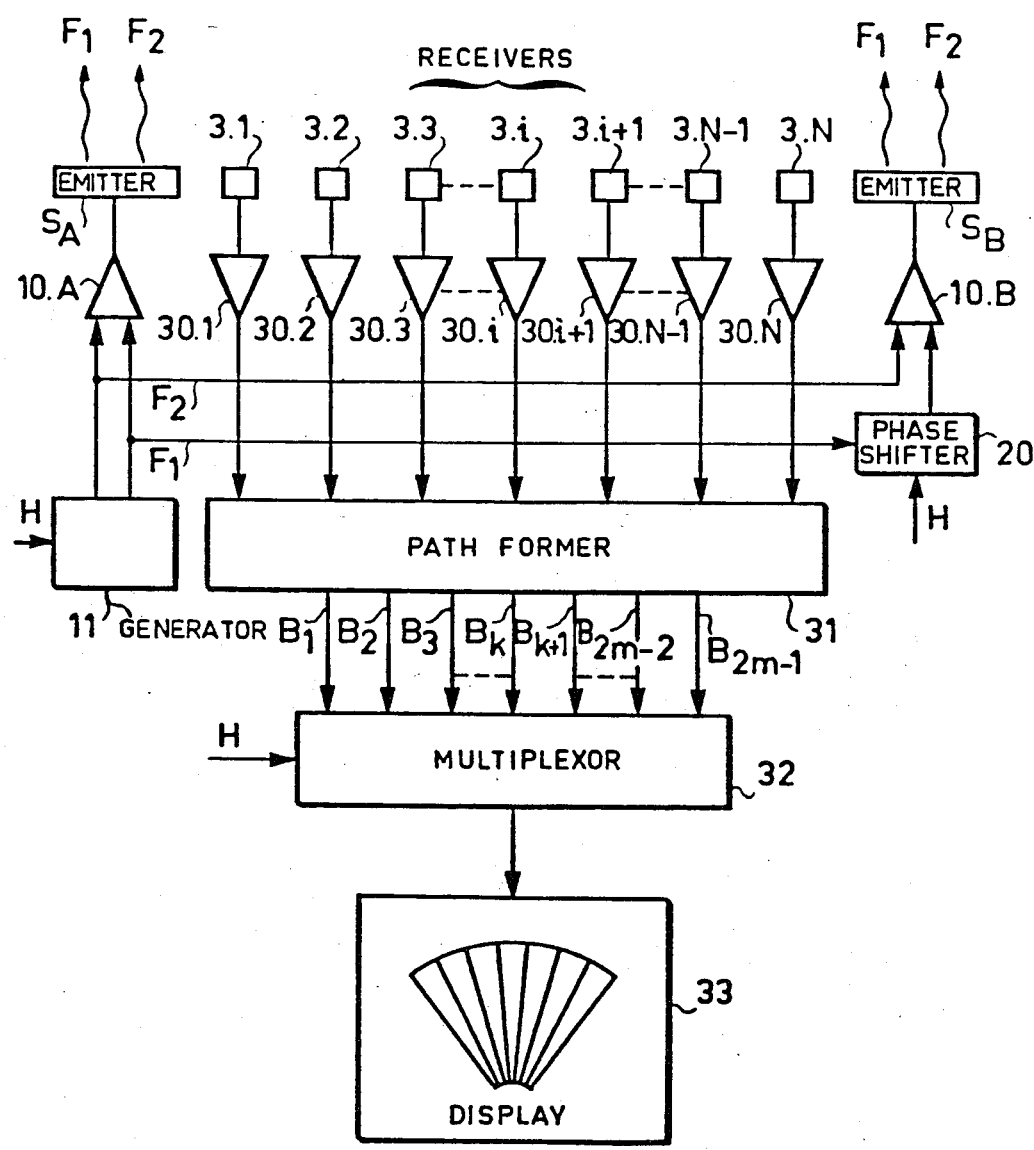
FIG. 6 illustrates a transmission-reception assembly in accordance with the invention.

FIG. 6 shows this embodiment in schematic form. Transmission takes place simultaneously from the two end transducers $S_A$ and $S_B$ at the frequencies $F_1$ and $F_2$.

At the frequency $F_2$, the signals emitted by the two transducers are continuously in phase. At the frequency $F_1$, however, the emitted signals are alternately in phase and in phase opposition in order to ensure that the same applies to the signals generated at the difference frequency $F_2 - F_1$.

During each of these sequences, $m - 1$ channels are formed, which permits surveillance of an angular sector without gaps.

The emission signals at the frequencies $F_1$ and $F_2$ are delivered by the generators 11. These signals are amplified by the amplifier 10.A and applied to the transducer $S_A$. The signal corresponding to the frequency $F_1$ is applied to a 0 or $\pi$ phase shifter controlled by a clock signal H. The signal delivered by the controllable phase shifter 20 is thus applied as well as the signal at the frequency $F_2$ to an amplifier 10.B. The amplified signals are applied to the transducer $S_B$.

The $\pi$ phase shift on the signal emitted by the transducer $S_B$ at the frequency $F_1$ produces said phase shift on the low-frequency signal which is present among the intermodulation products formed by the non-linear medium in the water cone located in front of the transducer $S_B$.

The power amplifiers 10.A and 10.B of said transducers make it possible to deliver a power output higher than one kilowatt per transducer. Said power output results in a high-frequency sound level of 125 dB per element (ref. IV/1 $\mu$B). Standard calculations in non-linear acoustics show that the resultant low-frequency sound level at 30 kHz will be of the order of 95 dB. The sources $S_A$ and $S_B$ therefore behave as two LF projectors at 30 kHz delivering a sound level of 95 dB (ref. IV/1 $\mu$B).

The receiving trasducer array comprises the N hydrophones 3.1, ... 3.i, ... 3.N. The signals received at the frequency $F_2-F_1$ are amplified by the amplifiers 30.1, 30.i ... 30.N and the amplified signals are applied to the channel formation circuits 31.

Formation of channels takes place in a known manner by phase-shift or time-lag of the signals and makes it possible to form a plurality of channels in parallel in different listening directions.

The 0 or $\pi$ phase shift by the circuit 20 is controlled by a clock signal H which also controls the low-frequency channel formation circuits. The channels $B_1$, $B_3$ are thus formed during one sequence and the channels $B_2$, $B_4$ are formed during the other sequence corresponding to the $\pi$ phase shift.

These channels are then detected and multiplexed by the circuit 32 in known manner and the signals delivered are applied to a visual display unit 33.

Consideration is given by way of example to N=7 hydrophones having a spacing of 3.5 $\Lambda$, where $\Lambda$ is the wavelength corresponding to the low frequency 30 kHz.

Figure 7:
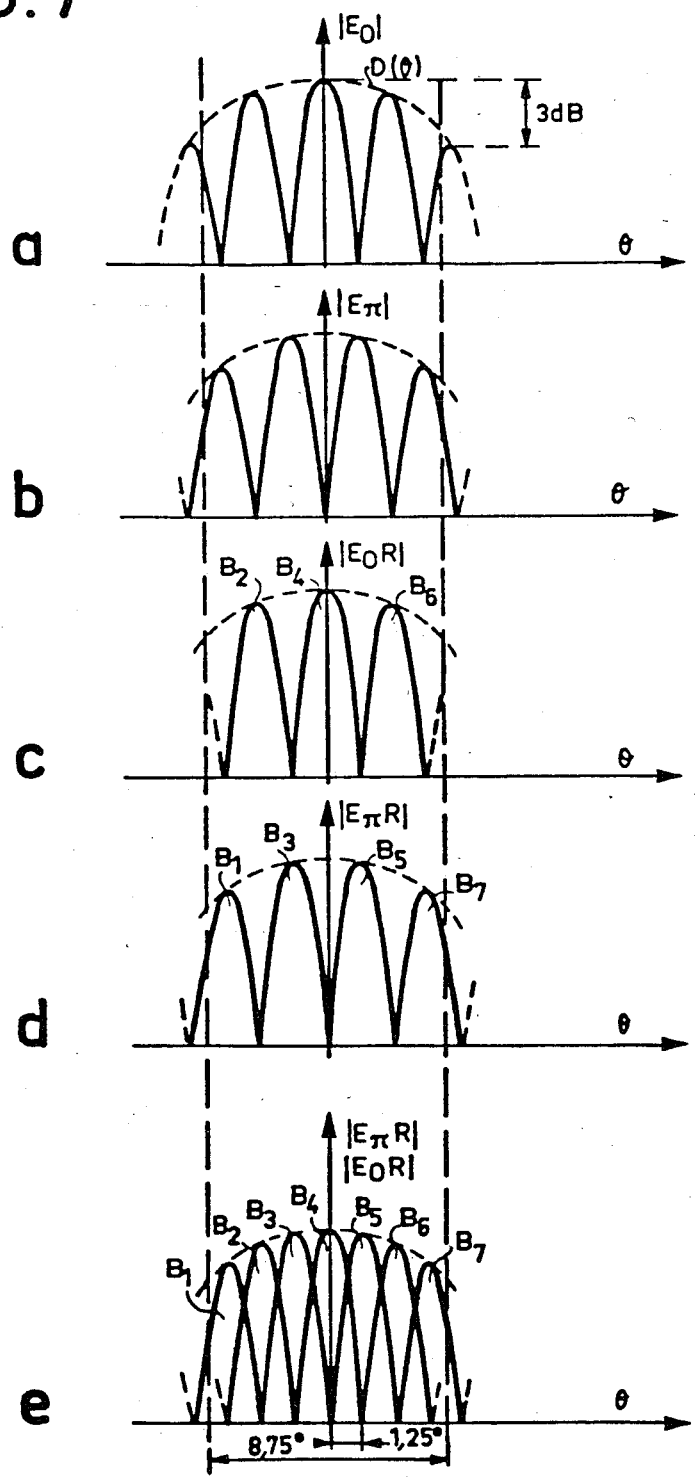
FIG. 7 provides diagrams of transmission and transmission-reception in the case of the different formed channels, in accordance with the invention.

FIG. 7 shows the diagrams thus obtained. On line a, there is shown the low-frequency transmission diagram ($E_o$) corresponding to low-frequency interferometry which gives the cosine lobes in accordance with relation (1) having a width of 1.25° at 3 dB ($L=171\lambda$) modulated by the transmission diagram of a transducer ($l=7\lambda$) at high frequency. On line b, there is shown the transmission diagram with a phase shift of $\pi$ at low frequency and $E\pi$ between the two transmissions. In this case, sine lobes are obtained in accordance with relation (4).

On line c, there is shown the transmission-reception diagram ($E_oR$) (zero phase shift) in which even-numbered channels $B_2$, $B_4$, $B_6$ are illustrated.

On line d, the diagram ($E\pi.R$) is shown with the odd-numbered channels $B_1$, $B_3$, $B_5$, $B_7$ ($\pi$ phase shift).

Finally, both the odd-numbered and even-numbered channels are shown on line e, from which it is apparent that the 8.75° sector corresponding to the HF diagram of transmission of a single transducer $D(\theta)$ is therefore covered.

It is possible in accordance with the invention to obtain a HF interferometer which is combined with the LF interferometer described in the foregoing but the HF receiving transducer array must be provided with a sufficiently large number of hydrophones to reject the image lobes beyond the listening sector corresponding to a transmission.

In the case of the example just given, the listening sector has an angle at the center of 8.75°, that is, a distance between receivers equal at a maximum to 6.57$\lambda$ at the frequency $F_1$ or $F_2$. In order to obtain a single HF and LF antenna, a distance equal to 5.83 between hydrophones is chosen, thus producing an antenna comprising thirty-one hydrophones, seven of which are used both for LF reception and for HF reception.

Figure 8:
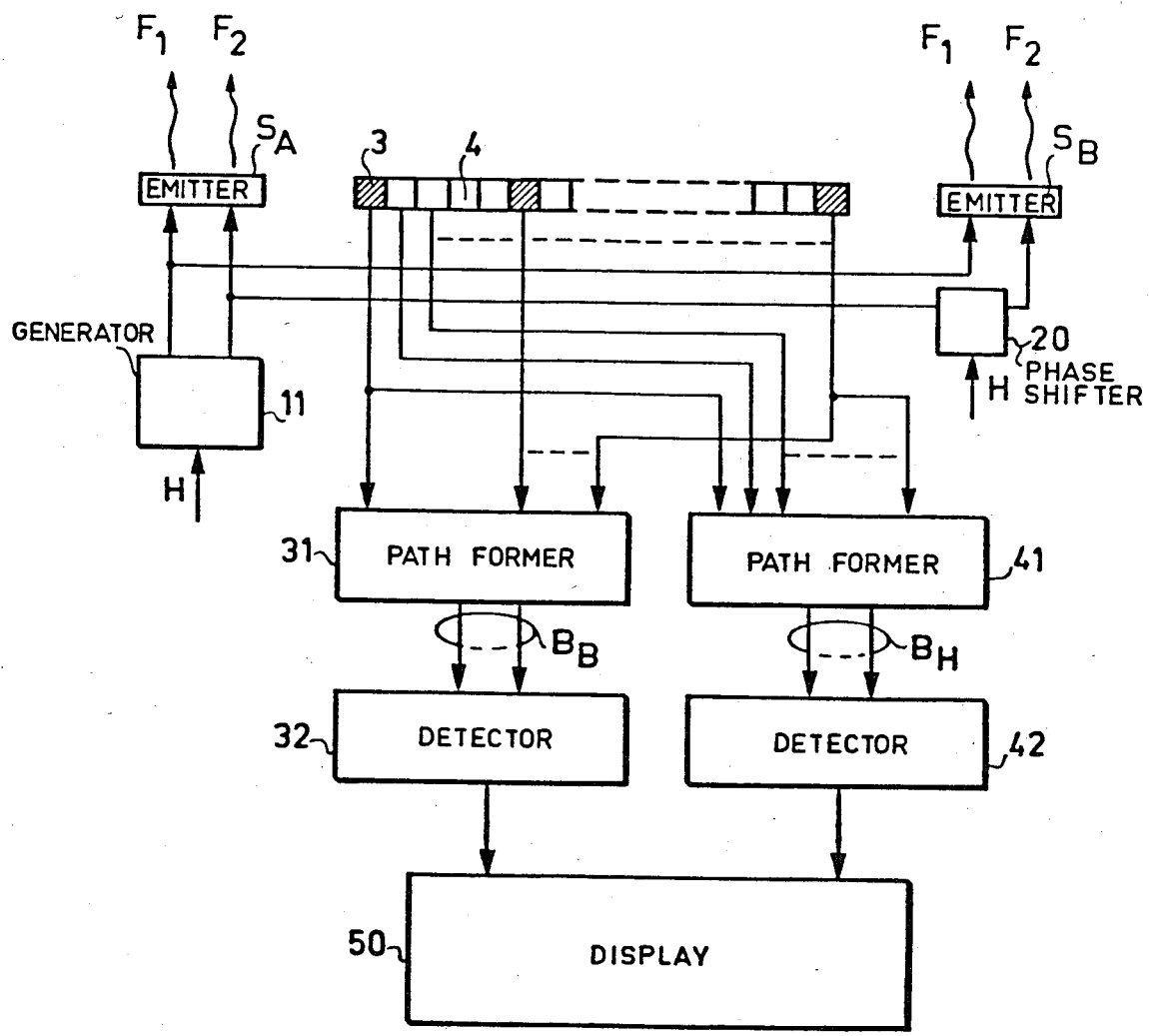
FIG. 8 is a diagram of a low-frequency and high-frequency transmission and reception assembly.

The system in which the two LF and HF interferometers are combined is shown in FIG. 8. There are again shown the LF interferometer elements, that is to say mainly the two sources $S_A$ and $S_B$ and the receiving transducer array, in which only the hydrophones such as the hydrophone 3 (that is to say one out of five) are taken into account in the LF channel formation unit 31.

The HF interferometer comprises the two sources $S_A$ and $S_B$ and the receiving antenna in which all the hydrophones such as those designated by the reference numerals 3 and 4 are taken into account in the HF channel formation unit 41.

After detection and multiplexing in the circuits 32 and 42, the two sets of formed HF and LF channels are sent simultaneously into a visual display unit 50 of the angular listening sector (azimuth-distance representation). A specific color is assigned to each set in order to distinguish between the HF and LF information for the purpose of comparison. To this end, a slight angular shift between the two sets is introduced in the visual display. It will be readily understood, however, that the HF and LF signals can be displayed separately.

In an alternative embodiment of the invention, two separate and distinct interferometer sonars are associated, namely an LF sonar as shown in FIG. 6 and a HF sonar as described in U.S. Pat. No. 4,234,939.

In another alternative embodiment of the invention, said LF interferometer sonar is associated with a conventional HF sonar which does not involve the use of interferometry.

What is claimed is:

1. An interferometric sonar in non-linear acoustics comprising:
    a sending transducer array including two transducers spaced at a distance L;
    means for supplying said two transducers with a first high frequency $F_1$ in phase and with a second high frequency $F_2$ alternately in phase and in phase opposition in which case said transducer array has an interferometric pattern which exhibits a set of peak values;
    a receiving transducer array having an array of transducers uniformly spaced between the sending transducers; and
    means for detecting the signals at a difference low-frequency $F_1-F_2$ which are received by the receiving transducer array, and for forming low-frequency channels centered on said peak values of the interferometric pattern.

2. A sonar according to claim 1, wherein the sending transducers have a length l and the distance L is substantially greater than said length l.

3. A sonar according to claim 1 further including visual display means, coupled to said means for detecting, for displaying an image representing signals of said low-frequency channels.

4. A sonar according to claim 3, wherein said receiving transducer array includes a number of transducers sufficient to form high-frequency channels, said means for forming the low-frequency channels is connected to a subassembly of said sending transducers, said receiving transducer array includes means connected to all the receiving transducers for detecting high-frequency signals and forming high-frequency channels, and said visual display means includes means for simultaneously displaying images corresponding to the low-frequency and high-frequency channels.

5. A sonar according to claim 4, wherein the visual display means make it possible to display the images corresponding to the low-frequency channels and high-frequency channels respectively in different colors and with a small angular shift.

6. A sonar according to claim 3, wherein the visual display means also displays signals delivered by a separate high-frequency interferometric sonar.

7. A sonar according to claim 3, wherein the visual display means displays signals delivered by a separate high-frequency sonar of a non-interferometric type.

* * * * *